(12) United States Patent
Shah

(10) Patent No.: US 8,992,863 B2
(45) Date of Patent: Mar. 31, 2015

(54) TISSUE PROCESSOR

(71) Applicant: Rushabh Instruments, LLC, Warrington, PA (US)

(72) Inventor: Preyas Shah, Warminster, PA (US)

(73) Assignee: Rushabh Instruments, Inc., Warrington, PA (US)

( * ) Notice: Subject to any disclaimer, the term of this patent is extended or adjusted under 35 U.S.C. 154(b) by 0 days.

(21) Appl. No.: 14/274,114

(22) Filed: May 9, 2014

(65) Prior Publication Data

US 2014/0248659 A1 Sep. 4, 2014

Related U.S. Application Data

(62) Division of application No. 13/323,134, filed on Dec. 12, 2011.

(60) Provisional application No. 61/422,772, filed on Dec. 14, 2010.

(51) Int. Cl.
| | |
|---|---|
| *A61B 10/00* | (2006.01) |
| *G01N 1/30* | (2006.01) |
| *G01N 1/31* | (2006.01) |
| *A01N 1/02* | (2006.01) |
| *G01N 35/00* | (2006.01) |
| *G01N 35/02* | (2006.01) |

(52) U.S. Cl.
CPC ............... *G01N 1/30* (2013.01); *G01N 1/312* (2013.01); *A01N 1/0242* (2013.01); *G01N 35/00732* (2013.01); *G01N 35/0092* (2013.01); *G01N 35/025* (2013.01)

USPC ............... 422/536; 422/63; 422/64; 422/65; 422/66; 422/67

(58) Field of Classification Search
CPC ............................. G01N 35/0092; B01L 9/00
USPC ............................................. 422/536, 63–67
See application file for complete search history.

(56) References Cited

U.S. PATENT DOCUMENTS

| | | |
|---|---|---|
| 4,141,312 A | 2/1979 | Louder |
| 4,421,246 A | 12/1983 | Schultz et al. |

(Continued)

OTHER PUBLICATIONS

International Search Report, dated Apr. 10, 2012 for International Application No. PCT/US11/064531, filed Dec. 13, 2011.

(Continued)

*Primary Examiner* — Jyoti Nagpaul
(74) *Attorney, Agent, or Firm* — RatnerPrestia

(57) ABSTRACT

A tissue processing system includes a plurality of processing stations. Each processing station includes a plurality of tissue receiving areas that are each configured to accommodate a tissue sample as well as physically isolate that tissue sample from other tissue samples at other receiving areas of the same processing station. Each processing station is configured to separately and individually process the tissue sample at each receiving area to either reduce or eliminate any potential for cross-contamination between the tissue samples undergoing processing at the same processing station. For each receiving area of each processing station, the system is configured to immerse a tissue sample at a particular receiving area in processing fluid for a pre-determined time according to a pre-defined protocol that is based upon parameters of that tissue sample.

7 Claims, 6 Drawing Sheets

(56) References Cited

U.S. PATENT DOCUMENTS

| | | |
|---|---|---|
| 4,604,964 A | 8/1986 | Gordon |
| 4,834,019 A | 5/1989 | Gordon |
| 5,681,530 A | 10/1997 | Kuster et al. |
| 6,080,365 A | 6/2000 | Thiem |
| 6,444,170 B1 | 9/2002 | Heid |
| 6,582,962 B1 | 6/2003 | Richards |
| 7,156,814 B1 | 1/2007 | Williamson, IV |
| 7,179,424 B2 * | 2/2007 | Williamson et al. .......... 422/536 |
| 7,329,533 B2 | 2/2008 | Fredenburgh |
| 7,541,161 B2 | 6/2009 | Fischer |
| 2005/0186114 A1 * | 8/2005 | Reinhardt et al. .............. 422/65 |
| 2007/0281364 A1 * | 12/2007 | Bogen et al. ................... 436/174 |
| 2010/0144018 A1 | 6/2010 | Shah et al. |
| 2010/0167943 A1 | 7/2010 | Adley et al. |

OTHER PUBLICATIONS

International Preliminary Report on Patentability, dated Mar. 20, 2014, corresponding to counterpart International Patent Application No. PCT/US2011/064531.

* cited by examiner

TISSUE PROCESSOR

CROSS REFERENCE TO RELATED APPLICATION

The application is a divisional patent application, which claims priority to U.S. Non-Provisional patent application Ser. No. 13/323,134, filed Dec. 12, 2011, and Provisional Patent Application No. 61/422,772, filed Dec. 14, 2010, the contents of which are incorporated by reference herein in their entirety.

FIELD OF THE INVENTION

The invention is generally directed to a tissue processor and the field of histology.

BACKGROUND OF THE INVENTION

A tissue processor automatically performs fixation, dehydration, cleaning, and paraffin impregnation of tissue samples (e.g., liver tissue, breast tissue, prostate tissue, etc.). At least two types of tissue processors exist, namely, chamber processors and station processors. A station-type processor includes a plurality of stations for processing the tissue samples, which are contained within individual cassettes. An example of a tissue cassette is disclosed in U.S. Pat. No. 4,421,246 to Schultz, which is incorporated herein by reference. The tissue cassettes are loaded into a single basket and taken from one station to the next station. In a chamber processor, tissue cassettes are loaded in a single enclosed chamber of the processor. The tissue cassettes remain stationary during processing in a fully enclosed retort while processing reagents and molten paraffin are moved to and from the chamber in a programmed sequence.

In both types of processors, all samples are immersed in a large reagent pool and cross-contamination of small tissue fragments may occur. Cross-contamination of the samples can skew the results of the tissue analysis. In view of the foregoing, there is a need to further refine tissue processors in the interests of reducing or eliminating cross contamination of tissue samples.

SUMMARY OF THE INVENTION

According to one aspect of the invention, a tissue processing system comprises a plurality of processing stations. Each processing station includes a plurality of tissue receiving areas that are each configured to accommodate a tissue sample as well as physically isolate that tissue sample from other tissue samples at other receiving areas of the same processing station. Each processing station is also configured to separately and individually process the tissue sample at each receiving area to either reduce or eliminate any potential for cross-contamination between the tissue samples undergoing processing at the same processing station.

According to yet another aspect of the invention, a method of individually processing tissue samples using a tissue processing system including a plurality of processing stations includes the steps of (i) receiving information corresponding to parameters of a tissue sample; (ii) positioning the tissue sample in a tissue receiving area of a processing station that is physically isolated from a different receiving area of the same processing station; (iii) processing the tissue sample according to a pre-defined protocol that is based upon the received parameters of the tissue sample; and (iv) transporting the tissue sample to another processing station of the tissue processing for further processing.

According to yet another aspect of the invention, a tissue processing system includes a first processing station, a second processing station, a plurality of carriers having at least two carrier types, the at least two carrier types including a first carrier configured to receive a first number of cassettes and a second carrier configured to receive a second number of cassettes, the first number of cassettes not equal to the second number of cassettes, a first dispenser for dispensing processing fluid in the first processing station and a second dispenser for dispensing fluid in the second processing station, and a controller configured to control the first and second dispensers to dispense fluid in the first and second processing stations, respectively, based upon received information corresponding to parameters of tissue samples that are docked at those stations.

According to yet another aspect of the invention, a tissue processing method includes positioning a tissue processing carrier in a processing station, the tissue processing carrier including an identifier identifying a number of cassettes in the tissue processing carrier, identifying the number of cassettes in the carrier, and dispensing fluid in the processing station on each of the identified number of cassettes.

The systems and methods described herein may significantly reduce or eliminate cross contamination of the tissue samples processed by the same system while providing comparable throughput of the tissue samples. Sample cross contamination may be significantly reduced or eliminate by dispensing processing fluid to individual cassettes that are isolated from one another. Processing fluid cross contamination may be significantly reduces of eliminated by collecting processing fluid runoff associated with the dispensing of the processing fluid for disposal. In accordance with one aspect of the present invention, systems and methods are described that utilize a small amount of processing fluid per cassette. This allows economical processing of the cassettes without the need to reuse fluids.

BRIEF DESCRIPTION OF THE DRAWING FIGURES

Figure 3A:
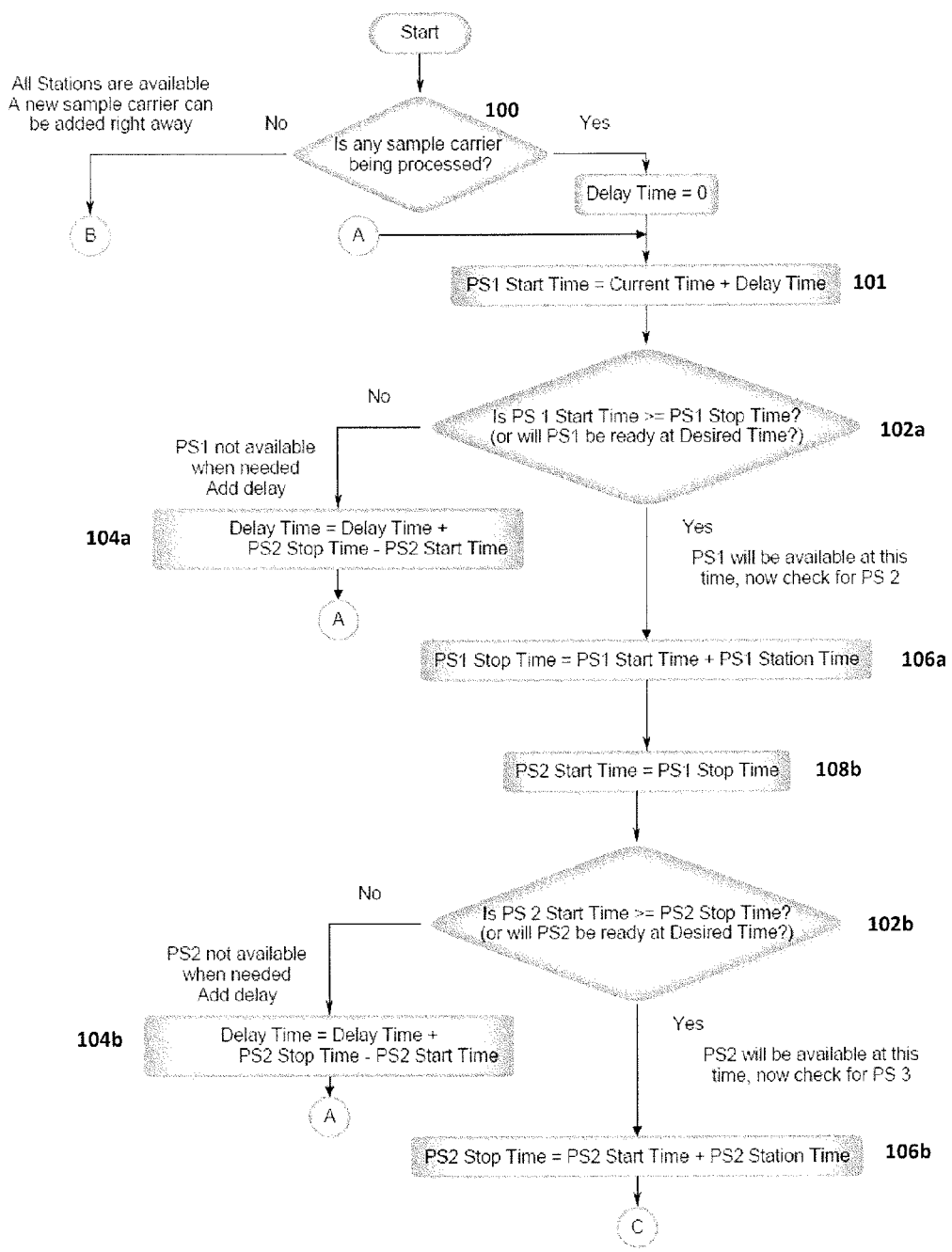
Figure 3B:
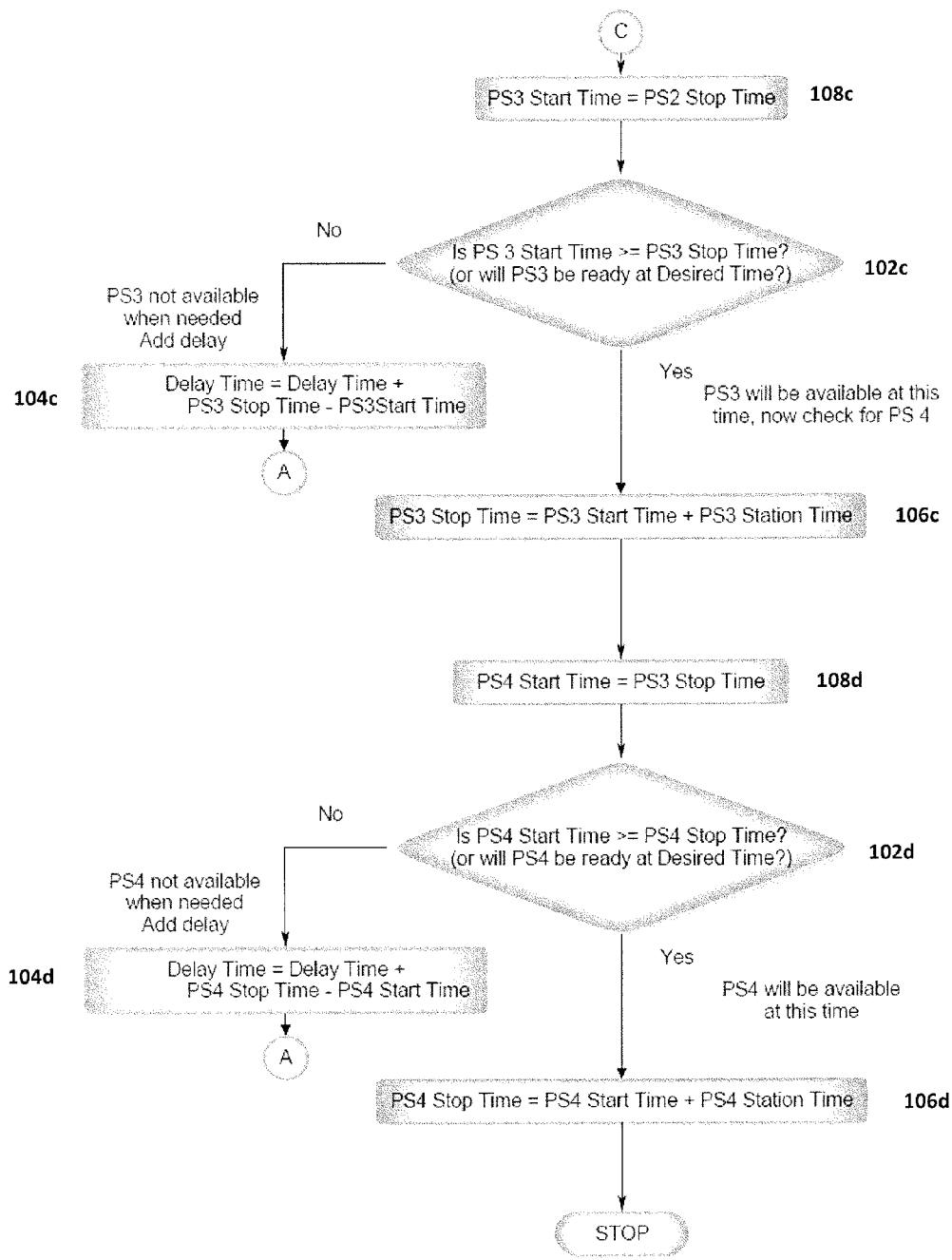
Figure 3C:
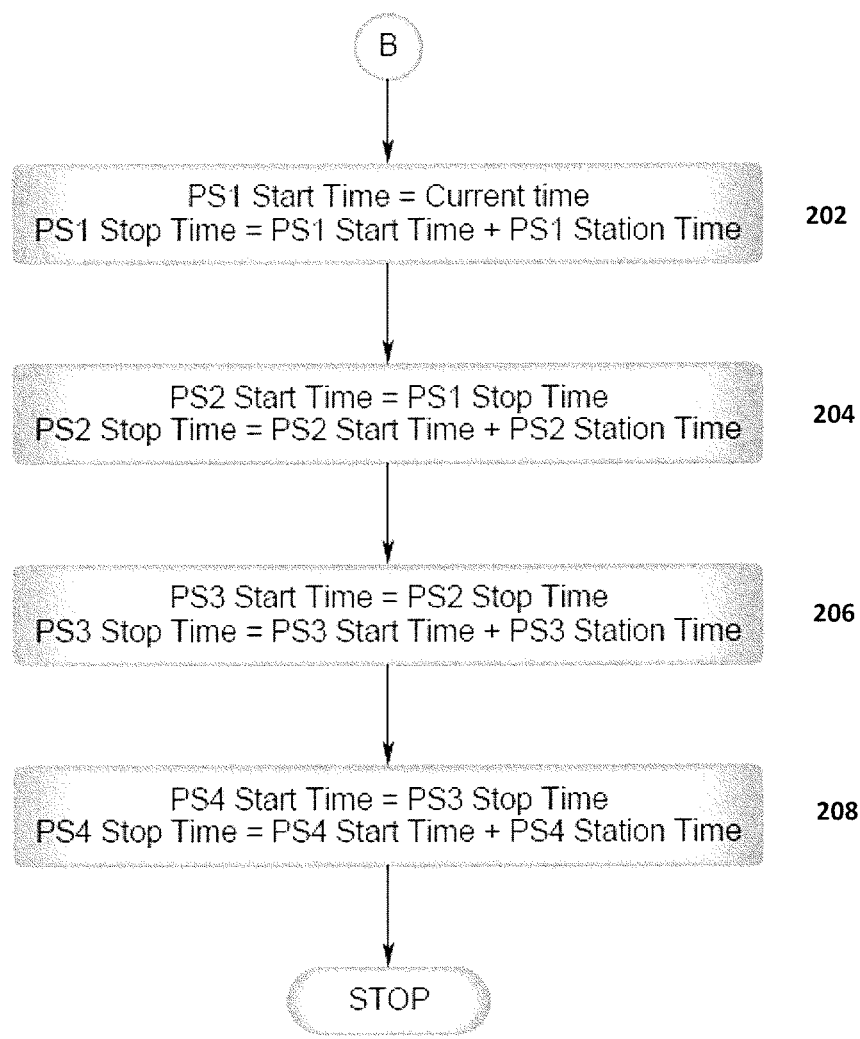

FIGS. 3A, 3B, and 3C depict a flowchart of exemplary steps for adding carriers to a tissue processing systems according to an aspect of the present invention.

Figure 4A:
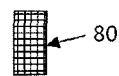
Figure 4B:
Figure 4C:
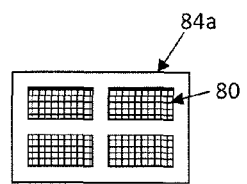
Figure 4C:
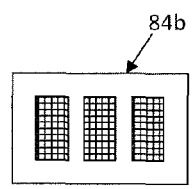
Figure 4C:
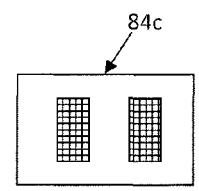
Figure 4C:
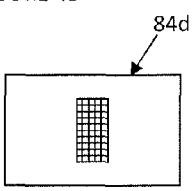
Figure 5:
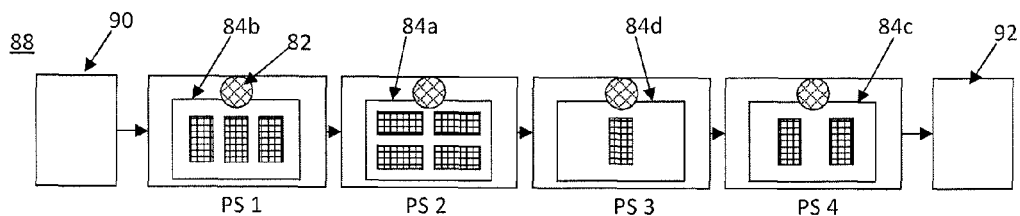

FIG. 4A depicts a tissue processing cassette icon;

FIG. 4B depicts a fluid dispenser icon;

FIG. 4C depicts a plurality of tissue processing carrier icons for carrying different numbers of cassette(s) (e.g., 1-4 cassettes) in accordance with an aspect of the present invention; and FIG. 5 depicts a tissue processing flow for processing carriers including different numbers of cassettes in accordance with aspects of the present invention.

DETAILED DESCRIPTION OF THE DRAWING FIGURES

Figure 1:
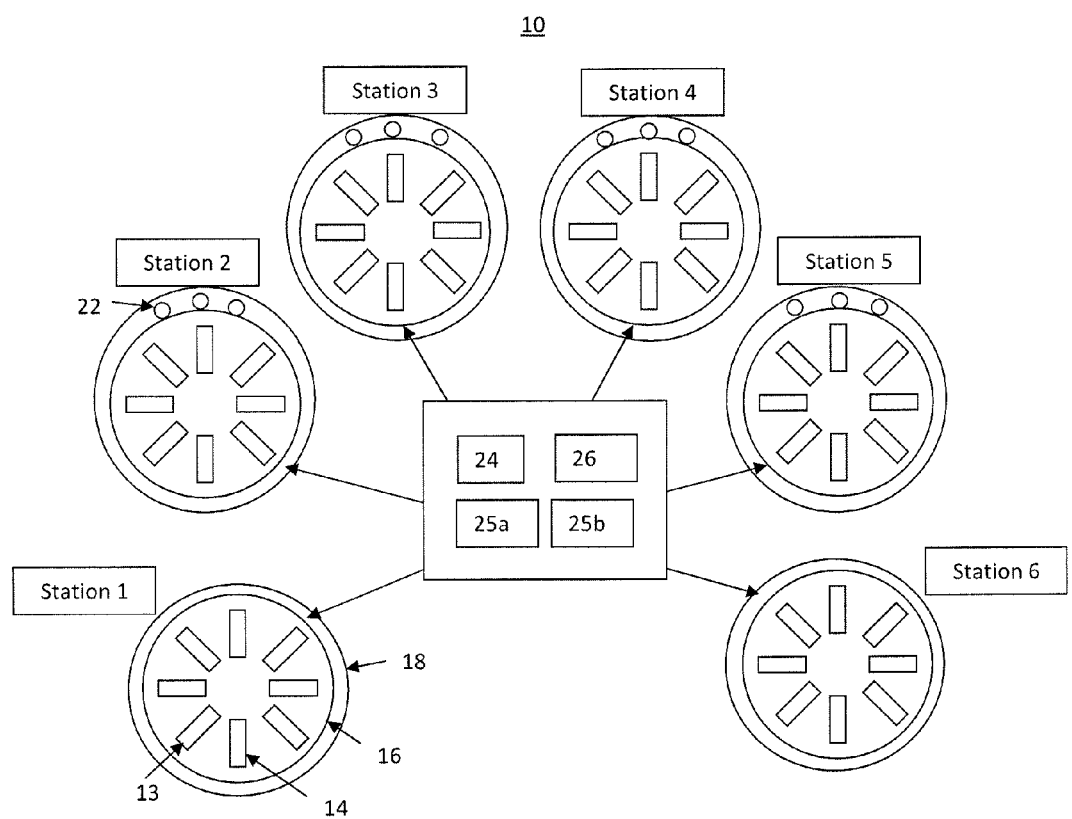
FIG. 1 depicts a schematic view of a tissue processing system for processing a tray of tissue samples, according to an exemplary embodiment of the invention.

FIG. 1 depicts a schematic view of a tissue processing system 10 (also referred to as a tissue processor) for processing a tray of tissue samples, according to an exemplary embodiment of the invention. The processor 10 disclosed in FIG. 1 is capable of processing tissues samples from multiple patients without introducing cross-contamination of the sample fragments or cross-contamination of reagents.

In this exemplary embodiment, each tissue sample (e.g., liver tissue, breast tissue, prostate tissue, etc.) is contained within a tissue cassette 12, and one or more cassettes 12 are positioned on a cassette tray/carrier 16. The cassette tray 16 includes a plurality of cassette receiving locations 13, each of which are sized to accommodate a tissue cassette 14. The cassette tray 16 defines an enclosed region for immersing the cassettes 14 in processing fluid (e.g., reagent or paraffin). The cassette trays 16 are preferably available in different sizes to accommodate different numbers of cassettes 14 (i.e., one tray may accommodate one cassette 14, whereas another tray may accommodate five cassettes 14). Thus, an operator may select one tray 16 for accommodating three cassettes 14, and a different tray 16 for accommodating ten cassettes 14.

The tissue processing system of FIG. 1 includes six stations (labeled Station 1 through Station 6) for processing one or more trays 16 carrying one or more tissue cassettes 14 (each cassette containing one or more tissue samples). According to the exemplary embodiment shown in FIG. 1, station 1 is a load station onto which a cassette tray 16 is loaded, stations 2-4 are reagent stations for processing the tissue samples within the tissue cassettes 14 of the tray 16, station 5 is a paraffin embedding station for embedding the cassettes 14 within paraffin, and station 6 is an unloading station. Those skilled in the art will recognize that the number of stations and the functionality of each station may differ from that described herein without departing from the spirit or scope of the invention. For example, according to an alternative exemplary embodiment, station 5 is a reagent station and station 6 includes an attachment mechanism for attaching an automated embedding system. As yet another alternative embodiment, station 6 may be a chilling station.

Referring still to the embodiment of FIG. 1, stations 1-6 each includes a base platform 18 with multiple cassette receiving locations 13 (eight in the illustrated embodiment) for receiving individual cassettes. Stations 2-5 each includes one or more fluid dispensers 22 for dispensing fluid (such as reagent or paraffin) into the tray 16 that is positioned on the base platform 18 in a particular location of a particular station, and a drain (not shown) through which the fluid may be expelled, when desired. In an exemplary embodiment, each station 2-5 is able to maintain a desired temperature of the tray 16, develop vacuum at the station (as needed per processing protocol requirements), develop pressure at the station (as needed per processing protocol requirements), and agitate the contents of the tray 16.

The mechanism for agitating the contents of the tray 16 may be a magnetic stirrer, for example. A magnetic stirrer employs a rotating magnetic field to cause a stir bar immersed in a liquid to spin, thus stirring it. The rotating field may be created either by a rotating magnet or a set of stationary electromagnets, placed beneath the tray. Alternatively, a circular track having different elevations may be positioned under one or more of the trays 16. As the tray 16 rotates, the different elevations cause the tray 16 to wobble, thereby agitating liquid within the tray 16. In yet alternative embodiment, the trays 16 may be agitated with ultrasonic energy or microwave energy in a manner that will be understood by one of skill in the art from the description herein.

To facilitate processing of the trays 16, the tissue processing system 10 includes a man-machine interface 24 to enable an operator to enter the parameters of each cassette tray, a transport mechanism 26 that transports the cassette trays between the stations, and a processor 25a for processing computer program instructions stored in a memory 25b (such as a non-transitory computer readable medium) to operate the stations and the transport mechanism 26 of the system according to a pre-defined protocol.

The man-machine interface 24 may include a keypad, a touch screen, and/or a bar code reader, to enable an operator to enter the parameters of each cassette tray 16. The parameters may include the number of cassettes 14 that are loaded on a particular tray 16, the type of tissue (e.g., liver tissue, breast tissue, prostate tissue, etc.) and the size or thickness of the tissue sample that is contained within each tissue cassette. Different tissues require different processing protocols. Based upon these parameters, the computer determines the appropriate protocol for processing that particular tray 16 of cassettes 14. By way of example, the protocol for processing a tray 16 of six cassettes 14 containing breast tissue may be 4 minutes at station 2 using 10 mL of fixative solution, 6 minutes at station 3 using 15 mL of dehydrant solution, 5 minutes at station 4 using 8 mL of clearant solution and 2 minutes at station 5 using 20 mL of paraffin. The foregoing values provided herein are exemplary.

The transport mechanism 26 comprises a mechanism that is capable of moving a tray between the various stations 1-6 The transport mechanism may be a single mechanism or multiple mechanisms translatable along X, Y and/or Z axes and rotatable about X, Y and/or Z axes to move a tray 16 between the various stations. In one embodiment, the transport mechanism 26 may comprise five independent transport mechanisms, each of which is positioned between respective adjacent stations to accomplish movement from one station to an adjacent station. The transport mechanism 26 may comprise any combination of a motor, belt, pulley, gear, arm, track, and spring, for example.

For example, the transport mechanism 26 may be a conventional robotic swing arm having gripping arms for grasping an individual cassette 14, an entire tray 16, and/or an individual cassette carrier (described with reference to FIG. 2), and transporting the cassette, tray and/or carrier between the processing stations 1-6.

The base platform 18 of each station 1-6 may optionally be translatable along X, Y and/or Z axes and rotatable about X, Y and/or Z axes for movement in concert with the transport mechanism 26. The stations 1-6 may be arranged in a row, or a semi-circle pattern (as shown in FIG. 1). The stations 1-6 may at least partially be enclosed by a fume hood incorporating a fume extraction fan for removing fumes.

According to one exemplary use of the tissue processor of FIG. 1, the tissue samples which are loaded on an individual tray 16 are preferably harvested from the same patient to eliminate cross-contamination between different patients. The cassettes 14 that are loaded on an individual tray 16 may optionally include the same tissue type (e.g., breast tissue). The operator first identifies the type of the tissue sample, the tissue sample size and/or thickness, and the number of cassettes 14 that are loaded in the sample tray 16. This information may be inputted into the system 10 via the man-machine interface 24. Based on the sample type, sample size, and number of cassettes 14 entered by the operator of the system 10, the system 10 generates the processing protocol for every station 1-6 that the tray 16 visits.

The processing protocol for each station 1-6 includes, for example, the processing time for each station and the volume of processing fluid (e.g., reagent or paraffin) that is to be dispensed at each station. The temperature level, the vacuum level and agitation at each processing station depends upon the of the processing station, i.e., the type of reagent or paraffin that is used at that station. The operator may program each station 1-6 to perform a specific processing task (e.g., establish station 1 as a fixative station and establish station 2 as a paraffin) via the man-machine interface 24 or each station 1-6 may be permanently dedicated for performing a specific processing task (e.g., station 1 is always a fixative station). The system is pre-programmed to set the temperature level, set the vacuum level and apply agitation at each station 1-6 depending upon the function of each station 1-6.

The operator then places the tray 16 on the base platform 18 of station 1. A sensor may be positioned on or adjacent the base platform of station 1 to sense the presence of the newly added tray at station 1. The sensor may be a pressure sensor, an optical sensor or a position sensor. The transport mechanism 26 of the system transports the tray 16 from station 1 to station 2. The reagent dispensers at station 2 dispense the pre-programmed amount of reagent into the tray 16, according to the parameters that were initially entered by the operator. The station 2 then agitates, e.g., gently rocks, the tray 16 while maintaining the temperature of the tray 16 and the level of vacuum applied to the tray 16 at the pre-programmed levels. Once the pre-programmed time has expired, the system 10 empties the reagent from the tray 16 into a waste container (not shown). The system 10 calculates the quantity of reagent (or paraffin) that is contained within the waste container, and prompts the operator to empty or replace the waste receptacle at the proper time. The various reagent waste streams are accumulated and recycled separately.

It is possible to program the system 10 such that it applies a reagent to the tray 16 for a fixed period of time, discards the reagent at the end of the period and then refills the tray 16 with fresh reagent again for another preprogrammed time. This process can be repeated multiple times, if so desired.

Once processing of the tray 16 at station 2 is complete, the transport mechanism 26 of the system transports the tray 16 from station 2 to station 3 for further processing. Once processing at station 3 is complete, the transport mechanism 26 of the system 10 transports the tray 16 from station 3 to station 4 for further processing. It should be understood that the description of the processing steps occurring at station 2 also apply to stations 3 and 4. According to one exemplary embodiment, station 2 is a fixative reagent station in which the tissues are immersed in a fixative solution (e.g., formalin), station 3 is a dehydrant reagent station in which the tissues are immersed in a dehydrant solution (e.g., alcohol), and station 4 is a clearant reagent station in which the tissues are immersed in a clearant solution (e.g., xylene).

Once processing of the tray 16 at station 4 is complete, the transport mechanism 26 of the system 10 transports the tray 16 from station 4 to station 5 for further paraffin embedding. At station 5, the station 5 delivers paraffin into the tray 16 to immerse the cassettes 14 in a paraffin bath. Once processing at station 5 is complete, the transport mechanism 26 of the system transports the tray 14 from station 5 to the unload station 6.

When the tray 16 arrives at the unload station 6, the system prompts the operator, either visually or audibly, to remove the processed tray 16 from the unload station 6. A sensor may be positioned on or adjacent the base platform of station 6 to sense the presence of the processed tray 16 at the unload station 6 after prompting. The sensor may be a pressure sensor, an optical sensor or a position sensor. If the sensor senses that the processed tray 16 has not been removed from station 6, the system 10 may be configured to prevent another processed tray 16 from advancing to station 6. Alternatively, the base platform 18 of station 6 may be configured to accommodate multiple trays. It should be understood that the functionality of each station 1-6 may vary from that described herein without departing from the scope or spirit of the invention.

The system is capable of processing multiple trays 16 simultaneously, i.e., processing one tray 16 at station 2, processing another tray 16 at station 3, and so forth, such that trays 16 may simultaneously undergo processing at each station. Simultaneous processing of multiple trays 16 results in faster turnaround time. To process multiple trays 16 simultaneously, the operator first informs the system 10 that a newly added sample tray 16 is waiting for processing by entering the parameters of the newly added tray 16 via the man-machine interface 24 (as described previously) and placing that new sample tray 16 at station 1. Based on the pre-programmed processing times for the newly added tray 16 and the pre-programmed processing times for the trays 16 which are undergoing processing at one or more stations 1-6 of the system 10, the transport mechanism 26 transports the newly added tray 16 to station 2 at the proper moment in time. The timing aspect of the process will be described next.

Because a delay in transporting a tissue sample from one station to the next station could have an adverse impact upon the processing of that tissue sample, the newly added tray 16 is moved to station 2 at the moment when the newly added tray 16 can advance from station to station without delay caused by the processing of another tray 16 at a later station. In other words, even though station 2 may be ready to receive the newly added tray 16, the system is configured to transport the newly added tray 16 to station 2 only when the newly added tray 16 can proceed through all of the stations without delay caused by a tray at stations 3-6.

Figure 2A:
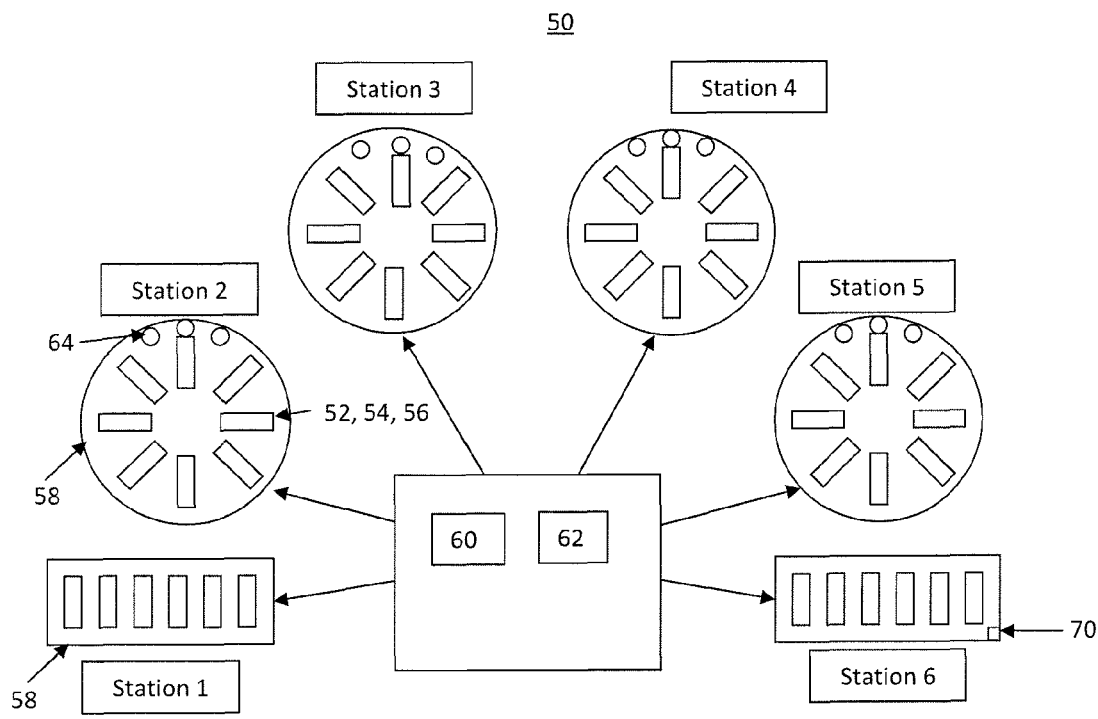
FIG. 2A depicts a schematic view of a tissue processing system for processing individual tissue samples, according to another exemplary embodiment of the invention.

FIG. 2A depicts a schematic view of a tissue processing system 50 that is configured for individualized processing of tissue samples that are positioned on a processing station, according to another exemplary embodiment of the invention. The tissue processing system 50 of FIG. 2A is similar to the tissue processing system of FIG. 1, and only the differences between those tissue processing systems are described hereinafter.

Figure 2B:
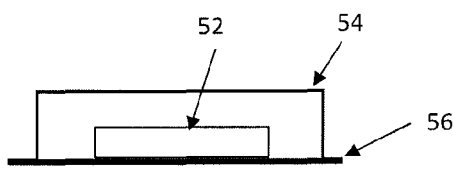
FIG. 2B depicts a cross-sectional view of a tissue cassette positioned in a cassette carrier that is docked at a cassette carrier location of a procession station.

In the system of FIG. 2A, each tissue cassette 52 is positioned in a cassette carrier 54 and each station 1-6 includes a plurality of cassette carrier locations 56 (also referred to herein as tissue receiving areas) that are each sized to accommodate a single cassette carrier 54. Thus, each station 1-6 can accommodate multiple cassette carriers 54. As shown in FIG. 2B, each tissue cassette 52 is positioned in a cassette carrier 54 and each cassette carrier 54 is docked at a cassette carrier location 56 of a station.

Each cassette carrier 54 accommodates one cassette 52 (unlike the tray 16 of FIG. 1 which accommodates multiple cassettes). The cassette carrier 54 is sized to contain a single tissue cassette 52 and is large enough to accommodate a limited volume of fluid, such as reagent or paraffin, into which the cassette 52 is immersed. The cassette carriers 54 are self-contained units that are physically isolated from each other on cassette carrier locations 56 of the base platform 58 of a station 1-6 to eliminate the potential for cross-contamination of the tissue samples on the same station. The tissue samples at any particular station 1-6 of the system 50 of FIG. 2 may be harvested from different patients without exposing the tissue samples at any station to cross-contamination.

The stations 2-5 of the system 50 are each configured for individualized processing of the cassettes 52 that are positioned at the cassette carrier locations 56 of each station 2-5. More specifically, each processing station 2-5 is capable of delivering fluid (e.g., reagent or paraffin) into a single cassette carrier 54 without delivering that fluid into another cassette carrier 54 that is also positioned on the same station. Each station 2-5 is capable of discarding the fluid in a single cassette carrier 54, as opposed to discarding the fluid in all of the cassette carriers 54 on the same station at the same time. Each station 2-5 is also capable of agitating individual cassette carriers 54, as opposed to agitating all of the cassette carriers 54 that are positioned on the same station 2-5 at the same time. Each station 2-5 is capable of controlling the temperature of the individual cassette carriers 54.

According to one exemplary use of the tissue processor of FIG. 2, the operator first identifies the type of the tissue sample that is contained within a cassette carrier 54. This information is input into the system via the man-machine interface 60 of the system 50. Based on the sample type and sample size entered by the operator of the system 50, the system 50 automatically generates the protocols for that cassette carrier 54 at each station 2-5. The protocols include at least the following for each station 2-5 of the system: the cassette carrier locations 56 into which the cassette carrier 54 will be delivered, the pre-programmed time, the temperature level, the vacuum level, and/or the quantity of reagent or paraffin to be dispensed.

The operator then places the cassette carrier 54 into a cassette carrier location 56 (also referred to as a tissue receiving area) on the base platform 58 of station 1. The transport mechanism 62 of the system 50 transports the cassette carrier 54 from a cassette carrier location 56 at station 1 to a pre-determined cassette carrier location 56 at station 2. Movement of the cassette carrier 54 from station 1 to station 2 may be accomplished by virtue of the transport mechanism 62 as well as rotation of the base platforms 58 of station 1 and/or station 2. The system is configured to remember the particular cassette carrier 54 location of station 2 in which the cassette carrier 54 is positioned.

The system then rotates the base platform 58 of station 2 to align the cassette carrier 54 with the fluid dispenser 64 of station 2. The fluid dispenser 64 at station 2 dispenses the pre-programmed amount of reagent (or any other fluid) into the cassette carrier 54, according to the parameters that were initially entered by the operator. The station 2 then agitates, e.g., gently rocks, the cassette carrier 54 while maintaining the temperature of the cassette carrier 54 and the level of vacuum applied to the cassette carrier 54 at the pre-programmed levels. Once the pre-programmed time has expired, the system tilts the cassette carrier 54 to discard the reagent into a waste container (not shown). Depending upon the protocol associated with the cassette carrier 54, the system 50 may be configured refill the cassette carrier 54 with fresh reagent again for another preprogrammed time. This process can be repeated multiple times. It should be understood that the cassette carrier 54 can undergo all of the above-described steps without impacting the processing of other cassette carriers 54 at station 2.

Once processing at station 2 is complete, the transport mechanism 62 of the system 50 then transports the cassette carrier 54 from station 2 into a pre-determined cassette carrier location 56 at station 3 for further processing. Once processing at station 3 is complete, the transport mechanism 62 of the system then transports the cassette carrier 54 from station 3 into a pre-determined cassette carrier location 56 at station 4 for further processing. Once processing at station 4 is complete, the transport mechanism 62 of the system 50 then transports the cassette carrier 54 from station 4 into a pre-determined cassette carrier location 56 at station 5 for further processing. It should be understood that processing steps described with reference to station 2 also apply to stations 3-5.

Once processing at station 5 is complete, the transport mechanism 62 of the system 50 transports the cassette carrier 54 from station 5 to a pre-determined cassette carrier location 56 at unload station 6. When the cassette carrier 54 arrives at station 6, the system 50 prompts the operator, either visually or audibly, to remove the processed cassette carrier 54 from the unload station 6. A sensor 70 may be positioned on or adjacent the base platform 56 of the unload station 6 to sense the presence of the processed cassette carrier 54 at the unload station 6. If the sensor 70 senses that the processed cassette carrier 54 has not been removed from station 6 by the operator, the system 50 may be configured to prevent another processed cassette carrier 54 from moving to station 6. Alternatively, the base platform 18 of station 6 may be configured to accommodate multiple cassette carriers (as shown in FIG. 2).

The system 50 is capable of individualized processing of multiple cassette carriers 54 at multiple stations 2-5. For example, three cassette carriers 54 can simultaneously undergo processing at station 2, while five cassette carriers 54 simultaneously undergo processing at station 3, and so forth. Individualized processing of multiple cassette carriers 54 at multiple stations 2-5 results in faster turnaround time of the tissue samples.

The system 50 employs an algorithm for simultaneously processing multiple cassette carries 54 at multiple stations 2-5. Because delaying the transport of a tissue sample from one station to the next station could adversely impact the processing of that tissue sample, a newly added cassette carrier 54 at station 1 is only moved to station 2 at the moment when the newly added cassette carrier 54 can advance from station to station without delay caused by the processing of another cassette carrier 54 at a downstream station. Using the algorithm, the system 50 determines the moment at which the newly added cassette carrier 54 moves from station 1 to a predetermined cassette carrier location 56 of station 2 as a function of (i) the processing protocol for the newly added cassette carrier 54, (ii) the number of available cassette carrier locations 56 at each station, and (iii) the processing protocol for the cassette carriers 54 which are undergoing processing at downstream stations of the system (i.e., stations 2-5). In other words, even though a cassette carrier location 56 at station 2 may be available to receive the newly added cassette carrier 54, the system 50 will transport the newly added cassette carrier 54 to its predetermined cassette carrier location 56 at station 2 only when the newly added cassette carrier 54 can proceed through all of the stations without delay caused by another cassette carrier 54 undergoing processing at any of stations 3-6.

FIGS. 3A, 3B, and 3C depict a flowchart of exemplary steps for scheduling/adding carriers to a tissue processing systems according to an aspect of the present invention. At decision block 100 of FIG. 3A, the system asks whether any sample carriers are being processed. If there is no sample carrier being processed, a new sample carrier's processing can start right away (i.e., go to 'B' in FIG. 3C). Once a sample carrier is scheduled to be processed, the Stop and Start Times for each Processing Station (PS) are calculated by the software in accordance with the equations 202, 204, 206 and 208 shown in FIG. 3C and retained in the memory.

When a next Sample Carrier is being loaded in the system, and the answer to decision block 100 of FIG. 3B is 'Yes', the software calculates the processing time at various stations based on the sample type and thickness. These processing times at various stations are used to calculate if a processing station will be done processing previously scheduled sample carriers when it is required to process this new sample carrier. More particularly, at decision blocks 102a-102d, each station is checked to determine whether a processing station will be done processing previously scheduled sample carriers when it is required to process this new sample carrier.

For each station, if a processing station will not be finished processing other sample carrier(s), the start of the processing of the new sample carrier is delayed according to equations 104a-104d. The calculated delay time for each processing station is added to the processing station 1 Start Time in accordance with equation 101. Once all four processing stations are available, the new sample carrier is scheduled for processing and the processing station availability times (Process Station Stop Time) are updated according to equations 106a-106d. The Process Station Start Times are then updated according to equations 108b-108d. It should be noted that the processing times at respective stations are derived as the Station Time for processing the tissue based on the sample type and thickness and the time to transport the sample is added to the processing time.

For an expanded system with multiple sample carrier capacity at each station, the software for the expanded system will be more complex compared to the software for single sample carrier processing at each station. Multiple levels of complexities can be added as described below.
  (a) Basic System: A system that will schedule one sample carrier at a time as it is loaded to ensure that the firs sample carrier loaded in will start the processing first.
  (b) Optimized System: A system that can optimize the throughput of the processed sample carriers once some are already being processed to see if by starting processing of a sample carrier that was loaded later can actually be processed sooner by delaying the start of some other slide carrier.
  (c) Flexible time optimized system: A system that may be programmed by the user to specify the flexibility of some processing times (e.g. longer formalin time at station 1 is okay or time at each station can be extended by a few seconds, etc.) to improve the overall throughput.
  (d) A system with more than one reagent dispenser at a given station: This system will have additional facility to remember when to discard the first reagent and add the next reagent within the station for a given sample carrier.

The scheme for the basic system forms the basis for the other two versions. This scheme follows the logic described above with more "house keeping" requirements at each process station.

Processing at each station may be as follows:
1. Initialize:
  a. set all positions as empty by setting the Stop Time for each position equal to the Current Time;
  b. set Station Stop Time equal to the Current Time; this variable identifies that there is at least one position is available for accepting a new Sample Carrier;
2. Scheduling a Sample Carrier:
  a. Check if the Station Stop Time is less than or equal to the Current Time.
    i. if it is, this indicates that at least one position is available at this Processing Station.
    ii. identify which position is available by checking the Stop Time for each position and the one with the earliest Stop Time is the one to allocate.
    iii. store the position number to be allocated and return the message that a position is available.
  b. if the station is not available, find out the earliest Stop Time. Store position number and set the Delay Time equals earliest Stop Time minus Current Time. Return the message that there are no positions available and a delay equals Delay Time will make one position available.
3. Once all processing stations report that a position will be available for the sample carrier if it started with the maximum required delay, each station will set up the Stop Time for the available position equals the Final Start Time for that station plus the Processing Time at that station.
4. When the Stop Time for a given position equals the Current Time, the processing for that sample carrier is completed and it needs to move to the next processing station. No further housekeeping for the position status will be necessary.

FIG. 4A depicts a tissue processing cassette icon 80 and FIG. 4B depicts a fluid dispenser icon 82. FIG. 4C depicts a plurality of tissue processing carrier icons 84a through 84d (referred to collectively as tissue processing carriers 84 or sample carriers 84 and generally as tissue processing carrier 84) for carrying different numbers of cassette(s) 80 (e.g., 1-4 cassettes) in accordance with an aspect of the present invention.

FIG. 5 depicts an alternative exemplary tissue processing system flow 88 for processing trays/carriers including different numbers of cassettes in accordance with aspects of the present invention. Different carriers are designed to carry a different number of cassettes. In an exemplary embodiment, each carrier includes one or more cavity(ies), with each cavity holding a cassette and providing some additional volume around and below each cassette that it is designed to hold. The system 88 allows each carrier to hold a different amount of reagent that will surround each cassette placed in it. Thus, a carrier that holds four cassettes will hold four times as much reagent volume as the reagent held by a carrier that holds only one cassette.

Each carrier can have a feature (for example a different hole pattern in a corner, or a bar code) to identify the number of cassette(s) and, optionally, their placement within the carrier.

The benefits of the system:
1. No reagent cross contamination since the fresh reagents may always used.
2. No sample cross contamination since the samples are never batched in accordance with one embodiment.
3. No over processing or under processing since each sample can be processed based on the most appropriate time durations based on the sample type and thickness as specified by the user.

A transport mechanism and a controller are not shown in the figure to facilitate depiction. The transport mechanism may include a conveyor for conveying the carriers from one processing station to the next.

The system 88 depicted in FIG. 5 shows multiple (i.e., six) stations—i.e., one load station 90, four processing stations (PS 1, PS 2, PS 3 and PS 4), and one unload station 92. Exemplary features/characteristics of each station in accordance with an exemplary embodiment are described below.

Load Station 90:

The operator may load one tissue processing carrier 84 at a time at the load station 90. The carrier 84 may have one or more cassettes 80. In the event there are more than one cassette 80 in a carrier 84, in an exemplary embodiment each cassette 80 in the carrier 84 will include sample from the same organ of the same patient having the same thickness. The carrier 84 may have a bar code that describes the details of the sample (e.g. ID, sample type and thickness). The load station 90 will detect a new sample carrier 84 being loaded by the operator and will prompt the user to enter the details of the sample. Alternatively, it can be equipped with a bar code reader that identifies the sample information automatically.

The load station 90 may have sufficient storage space for more than one sample carrier 84 and means to transport the sample carrier 84 from one position to the next (for example a conveyer or a carousel) until the sample carrier 84 is transported to the first processing station (PS1).

The system software decides when the processing for the sample can begin. Once the start time for the processing is reached, the system will move the sample from the Load Station to the first processing station, PS1.

In an exemplary embodiment, the system can process sample carriers 84 with different combinations of different number of cassettes 80, different types of sample and samples of different thickness simultaneously.

Processing Station (PS1 through PS4):

Each processing station PS1-PS4 may have one or more reagent dispensers 82. Each processing station PS1-PS4 will dispense one type of reagent. Typically, reagent dispensers at PS1 will have a fixative (e.g. formalin), at PS2 it will have a dehydrant (e.g. alcohol), at PS3 it will have a clearant (e.g. xylene) and at PS4 it will have the embedding media (e.g. paraffin). In an exemplary embodiment, one or more of the processing station (e.g., all) can develop vacuum inside the station PS1-PS4 if required for processing the tissue, maintain a desired temperature for processing the tissue, and/or provide agitation to the sample carrier 84 for better mixing of the sample with the reagent for improved processing. Alternate means of mixing may include using ultrasonic energy or using microwave energy.

The system will determine the amount of reagent to be dispensed based on the number of samples/cassettes 80 and also based on the pre-determined reagent quantity to be dispensed per sample. For example, the system may have been programmed to dispense 5 ml of reagent at PS1 for every sample and if a sample carrier with 3 cassettes is being processed, the system will dispense 15 ml of reagent.

A processing station PS1-PS4 may have more than one reagent dispenser 82 to dispense same type of reagent but of different concentration. For example at PS 2, there may be three dispensers one for 50% alcohol, one with 80% alcohol and a third one with 100% alcohol.

Once the processing time for the given reagent for a specific type and thickness of the sample is over, the system will collect the reagent from the sample carrier in a waste collector at the processing station, e.g., to eliminate the possibility of fluid cross contamination. The collected reagent may then be refined, recycled for re-use, or discarded. In contrast, many conventional systems automatically redistribute recycled reagent to the various stations, which can cross-contaminate the tissue samples at those stations.

If the processing station PS1-PS4 has only one reagent dispenser 82, the sample carrier 84 is taken to the next processing station. For a system with more than one reagent station, a subsequent reagent dispenser 82 dispenses the next reagent at the same processing station until every reagent has been dispensed and mixed with the sample once. At the end of mixing with the last reagent, the sample carrier 84 will be transported to the next processing station.

In an exemplary embodiment, the user will have an option to decide if the last reagent (typically paraffin) at the last station (PS4) will be discarded or not before transporting the Sample carrier to the Unload Station.

Unload Station 92:

Unload station 92 may be a temperature controlled station. This station will continue to collect the sample carriers 84 as their processing is completed at PS4. This station will alert the user when the sample is ready for pick up. The system will not transfer any more samples from PS4 to the unload station 92 if there is no more room to hold one more sample.

Processing Method:

A sample carrier 84 with a known number of cassettes is loaded at the load station 90 by the operator. The operator enters the number of cassettes 80, and the information about the sample. This information can include the sample ID, type of sample (e.g. prostate, breast, brain, etc.) and the thickness of the sample (e.g. 2 mm, 3 mm, etc.). Alternatively, a bar code applied to the carrier 84 may contain the same information and the system will read that information from the bar code.

Based on the sample type, the thickness of the sample(s) and the number of cassettes 80, the system 88 decides the processing time and the quantity of processing fluid that is required at each of the processing stations. These processing parameters may have been entered by the user prior to loading samples or may have been programmed at the factory and may have been subsequently modified by the operator. For example, a sample carrier 84 with one 2 mm prostate sample cassette 80 may receive 5 ml of reagent, one with two cassettes 80 may receive 8 ml, and one with three cassettes 80 may receive 11 ml.

Next, the system 88 calculates the start time for processing the sample such that each of the Processing Stations PS1-PS4 will be available when needed. An algorithm to perform this calculation is described above.

Although this invention has been described with reference to particular embodiments, it will be appreciated that many variations may be resorted to without departing from the spirit and scope of this invention. For example, the number of stations and the functionality of each station may vary from that described herein without departing from the scope and the spirit of the invention.

What is claimed:

1. A method of individually processing tissue samples using a tissue processing system including a plurality of tissue processing stations comprising the steps of:

receiving information corresponding to parameters of a first tissue sample;

receiving information corresponding to parameters of a second tissue sample;

positioning the first tissue sample in a tissue receiving area of a processing station that is physically isolated from a different tissue receiving area of the same processing station;

positioning the second tissue sample in a second tissue receiving area of the processing station that is physically isolated from the first tissue receiving area of the same processing station;

processing the first tissue sample according to a pre-defined protocol that is based upon the received parameters of the first tissue sample, wherein the processing step comprises (i) dispensing processing fluid including either reagent solution or paraffin to immerse the first tissue sample in the processing fluid for a pre-determined time based upon the pre-defined protocol, and (ii) exposing the first tissue sample to vacuum and/or pressure so that the fluid permeates the first tissue sample;

processing the second tissue sample according to a pre-defined protocol that is based upon the received parameters of the second tissue sample, wherein the pre-defined protocol of the second tissue sample differs from the pre-defined protocol of the first tissue sample that is positioned in the same processing station; and processing the first and second tissue samples that are positioned in the same processing station at the same time; and transporting the first tissue sample to a tissue receiving area of a second processing station of the tissue processing system for further processing.

2. The method of claim 1, further comprising the step of:
collecting processing fluid runoff associated with the dispensing step to eliminate fluid cross contamination.

3. The method of claim 1, wherein the processing steps each comprise applying heat or agitation to the tissue samples at the processing station depending upon the processing fluid used at that station.

4. The method of claim 1, further comprising the step of processing another tissue sample that is positioned in a different tissue receiving area of the same processing station according to a different protocol such that processing times for the first tissue sample and said another tissue sample can differ.

5. The method of claim 1, wherein prior to the positioning steps, the tissue processing system performs the step of determining a time when the first tissue sample can undergo processing in each of the processing stations without being delayed by another tissue sample undergoing processing.

6. The method of claim 1, wherein the transporting step further comprises transporting the first tissue sample to the second processing station only when the first tissue sample can be processed by the second processing station and later processed at a third processing station without any delay caused by another tissue sample at the second processing station and yet another tissue sample at the third processing station.

7. The method of claim 1, wherein the parameters of a tissue sample include tissue size and tissue type.

* * * * *